United States Patent [19]
Woodard

[11] Patent Number: 6,013,060
[45] Date of Patent: Jan. 11, 2000

[54] INTRAVENOUS LIQUID FLOW REGULATOR

[76] Inventor: Robert W. Woodard, R.R. 2 Box 94, Frankfort, Kans. 66427

[21] Appl. No.: 08/974,110

[22] Filed: Nov. 19, 1997

[51] Int. Cl.⁷ .................................................. A61M 5/00
[52] U.S. Cl. ........................... 604/246; 604/122; 604/126
[58] Field of Search .................... 604/246, 122, 604/126, 123, 124, 265, 266

[56] References Cited

U.S. PATENT DOCUMENTS

| | | | |
|---|---|---|---|
| 3,827,562 | 8/1974 | Esmond | 210/304 |
| 3,833,013 | 9/1974 | Leonard | 137/171 |
| 4,177,808 | 12/1979 | Malbec | 128/214 R |
| 4,237,880 | 12/1980 | Genese | 128/214 G |
| 4,355,638 | 10/1982 | IWatschenko et al. | 128/214 F |
| 4,413,990 | 11/1983 | Mittleman | 604/122 |
| 4,722,732 | 2/1988 | Martin | 604/132 |
| 4,775,482 | 10/1988 | Thurman | 210/668 |
| 4,861,617 | 8/1989 | Pall et al. | 604/122 X |
| 4,898,581 | 2/1990 | Iwatschenko | 604/122 |
| 4,994,022 | 2/1991 | Steffler et al. | 604/7 |
| 5,562,638 | 10/1996 | Severs | 604/266 |
| 5,674,200 | 10/1997 | Ruschke et al. | 604/126 |

*Primary Examiner*—John D. Yasko
*Attorney, Agent, or Firm*—Kenneth W. Iles

[57] ABSTRACT

An I.V. bag is connected to a drip chamber, then to a conventional tube clamp and a regulating tube containing a wick or other material that breaks surface tension of the liquid in the tube, which flows into a bubble separator that forces any remaining entrained air through one or more hydrophobic gas permeable membranes, and then into the patient. A check valve near the patient prevents back flow. A vent placed adjacent to the tube clamp isolates any pressure drop above the vent, allowing a pressure head to develop in the regulating tube, which insures a constant flow of I.V. liquid into the patient regardless of downstream or upstream hydraulic conditions.

18 Claims, 5 Drawing Sheets

INTRAVENOUS LIQUID FLOW REGULATOR

BACKGROUND OF THE INVENTION

1. Field of the Invention

The present invention is related to an apparatus and process for regulating the rate that liquid flows through an intravenous (I.V.) set used to infuse liquids and drugs into humans and animals. More particularly, the present invention is directed to an I.V. liquid flow regulator that uses a wick and a vertical tube clamp to regulate the rate of flow.

2. Description of Related Art Including Information Disclosed Under 37 C.F.R. Sections 1.97–1.99

Regulating the rate of flow through an I.V. set into a patient to achieve a desired or necessary rate of infusion of liquid or dissolved drugs is sometimes critical to successful patient treatment. Conventional I.V. sets alone do not regulate the rate of flow of liquid through them and into the patient. In these, after an initial air purge and set up, the operator adjusts the tube clamp to give the desire liquid flow setting. The conventional tube clamp is in effect a simple variable orifice device that roughly regulates the flow of liquid by squeezing the tube more or less tightly. Therefore, changes in either the upstream or downstream hydraulic conditions (as gauged from the tube clamp) will cause changes in the flow rate across the orifice. The upstream fluid head will gradually change as the fluid height in the I.V. bag or container slowly decreases. Because of the size of the container, however, and the relatively low flow rate, the change of flow rate due to the change of column height in the I.V. bag or container is slow and predictable. The change in flow rate below the tube clamp, however, has the largest unpredictable effect on the flow rate. Patient movement, such as rolling over, lifting an arm, standing, walking, sitting up and the like can cause significant changes in the patient's blood pressure, which substantially changes the rate at which the liquid will be infused into him. Further, by moving, the patient can clamp, or unclamp the vein that the catheter enters, changing the back pressure on the liquid in the I.V. set. Any movement, or even change in certain patient physiology, effectively alters the back pressure into which the catheter discharges. Additional, movement of the patient can cause the tube running to the catheter to be pinched or unpinched, changing the local flow restriction of the transport tube and the local pressure of liquid upstream of the catheter.

Changing any of these downstream conditions ultimately changes the pressure drop across the tube clamp of a common I.V. set, thus changing the flow rate from the desired settings.

Currently a number of different infusion pumps designed to provide a certain defined rate of flow and therefore infusion through an I.V. set are in use. The majority of these pumps use a roller pump designed to work against the plastic tubing of the I.V. set. Although these devices work well, they are quite expensive and can serve only one patient at a time.

Therefore, a demand exists for an I.V. liquid flow regulator that is simple, reliable, easy to manufacture and relatively inexpensive to the ultimate consumer.

SUMMARY OF THE INVENTION

Accordingly, it is a primary object of the present invention to provide an I.V. liquid flow regulator that is simple in use and manufacture.

It is another object of the present invention to provide an I.V. liquid flow regulator that is reliable.

It is another object of the present invention to provide an I.V. liquid flow regulator that is inexpensive to the ultimate consumer.

These and other objects of the present invention are achieved by providing a vent directly below the conventional tube clamp. The vent is open to the air, but includes a means for preventing contamination of the I.V. liquid through the vent. By venting the regulating tube, the pressure drop of the I.V. system above the vent is isolated from the regulating tube. This arrangement allows the pressure head in the regulating tube to control the rate of flow of liquid through the I.V. liquid flow regulator. A wick of predetermined size and absorption characteristics inside the tube downstream of the tube clamp prevents the formation of bubbles in the transport tube under all normal conditions and a bubble separator further downstream removes any bubbles that may have been entrained in the system.

Other objects and advantages of the present invention will become apparent from the following description taken in connection with the accompanying drawings, wherein is set forth by way of illustration and example, the preferred embodiments of the present invention and the best mode currently known to the inventor for carrying out his invention.

DETAILED DESCRIPTION OF THE PREFERRED EMBODIMENTS

As required by the Patent Statutes and the case law, the preferred embodiment of the present invention and the best mode currently known to the inventor for carrying out the invention are disclosed in detail herein. The embodiments disclosed herein, however, are merely illustrative of the invention, which may be embodied in various forms. Therefore, specific structural and functional details disclosed herein are not to be interpreted as limiting, but merely to provide the proper basis for the claims and as a representative basis for teaching one skilled in the art to which the invention pertains to make and use the apparatus disclosed herein as embodied in any appropriately specific and detailed structure.

Figure 1:
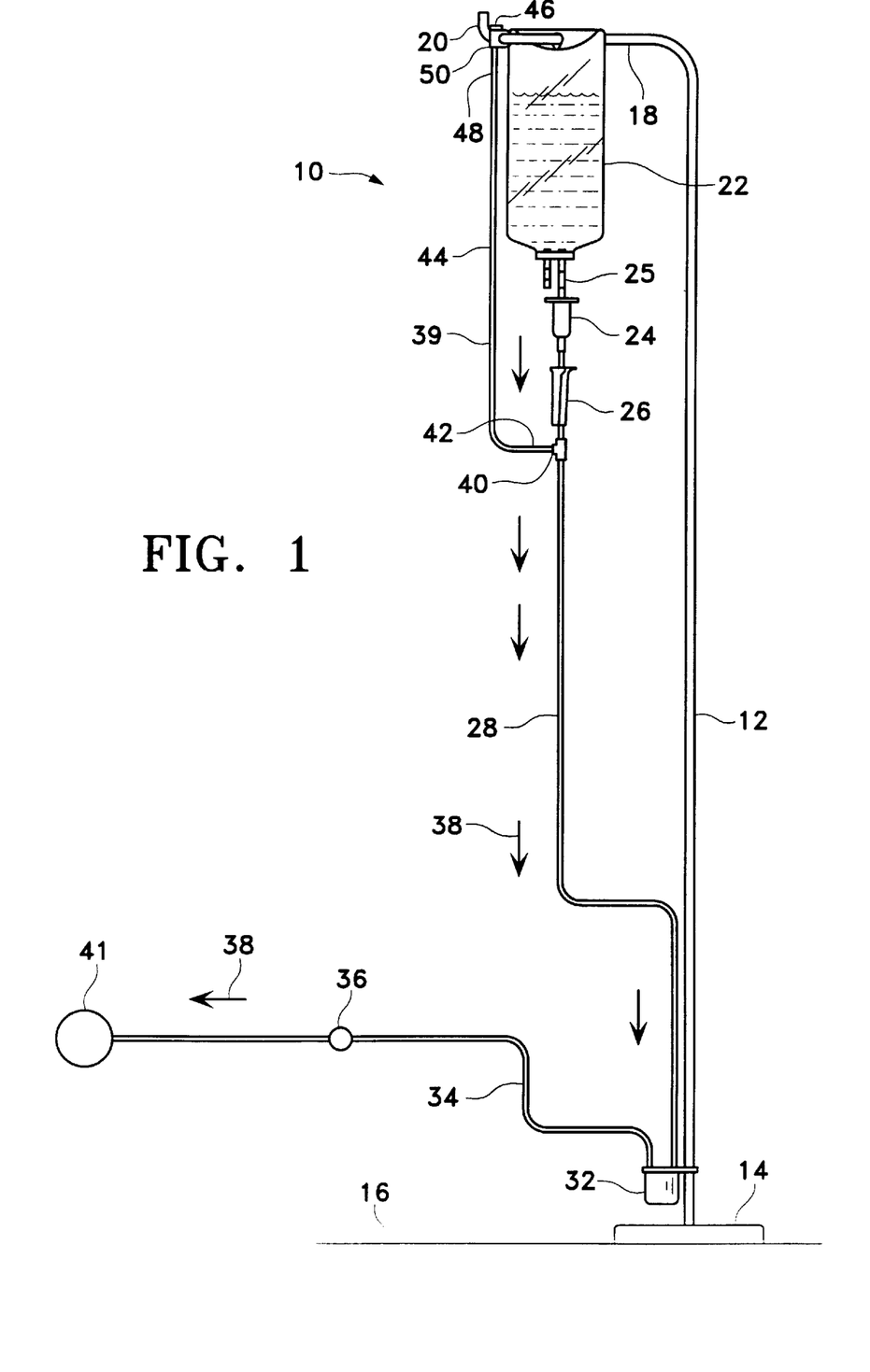
FIG. 1 is a side elevation of an intravenous liquid flow regulator according to the present invention set up for use.
Figure 2:
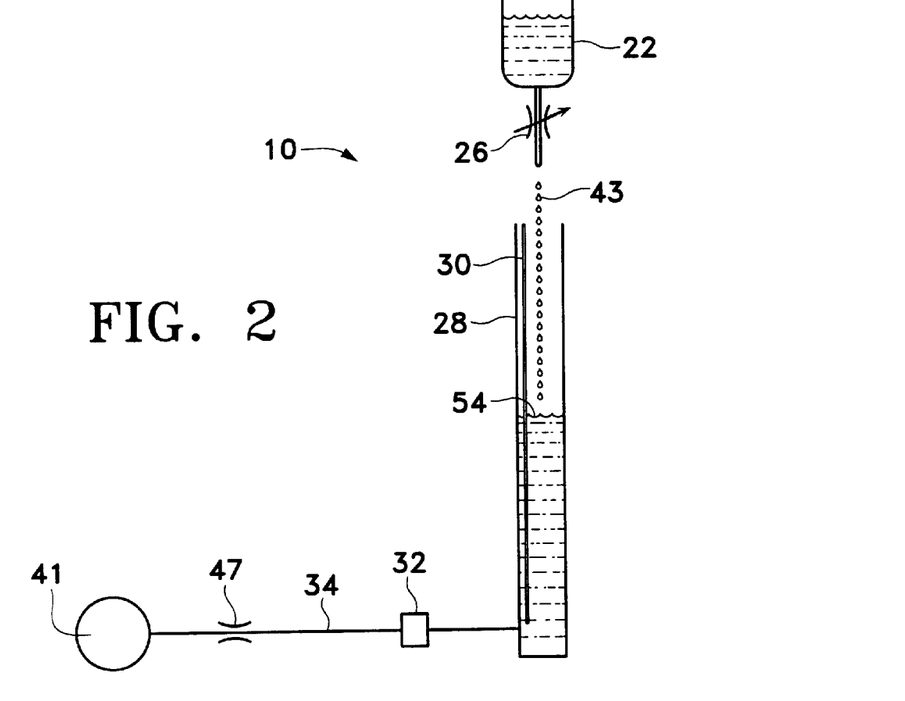
FIG. 2 is a schematic view of the intravenous liquid flow regulator of FIG. 1.

Referring now to FIGS. 1 and 2, there is shown an intravenous liquid flow regulator 10. A stand 12 having a base 14 is set onto the floor 16 or other supporting surface. The stand 12 includes a horizontal arm portion 18 and an upwardly bent hook 20 on the distal end of the horizontal arm portion 18. The stand 10, arm 18, and upwardly bent hook 20 are conventionally made from a single length of rod. A conventional I.V. bag or other container 22 is conventionally suspended from the horizontal arm 18. A drip chamber 24, for directly or indirectly measuring the rate of liquid flow through the regulating tube 28 is conventionally connected to an outlet tube 25 of the I.V. bag 22 at the bottom of the I.V. bag 22 with the puncture tube in the drip chamber 24 inserted into the gland 25 of the I.V. bag or container 22. A regulating tube 28 having an internal wick 30 (see FIG. 2), or other means for reducing or eliminating the formation of bubbles in the regulating tube 28. A conventional tube clamp 26 is connected to the regulating tube 28 at a point below the drip chamber 24 and is used to set the desired liquid flow rate.

The regulating tube 28 extends downwardly from the drip chamber 24 to a point near the floor 16, which may be lower than the level at which the I.V. finally enters the patient 41. The regulating tube 28 passes into a bubble separator 32, which may be clamped to a lower end of the stand 12 at a point near the floor 16. The bubble separator 32 forces any gas that may have become entrained in the liquid flowing through the regulating tube 28 into the atmosphere, insuring that no gas is transfused into the patient 41. A transport tube 34 carries the liquid from the bubble separator 32 to the patient 41, where the liquid is infused through a conventional catheter or venipuncture device 47. A check valve 36 in the transport tube 34 prevents liquid from flowing backward from the patient 41 into the intravenous liquid flow regulator 10. The desired or normal direction of flow of liquid through the intravenous flow regulator 10 is shown by the arrows 38.

A vent 39 includes, in one embodiment, a vent tee 40 inserted into the regulating tube 28 below and adjacent to the tube clamp 26. A proximal end 42 of a vent tube 44 is connected to the tee portion of the vent tee 40. A vent filter 46 is inserted into a distal end 48 of the vent tube 44, which is attached to the horizontal arm portion 18 of the stand 12 by the vent tube clip 50.

Figure 6:
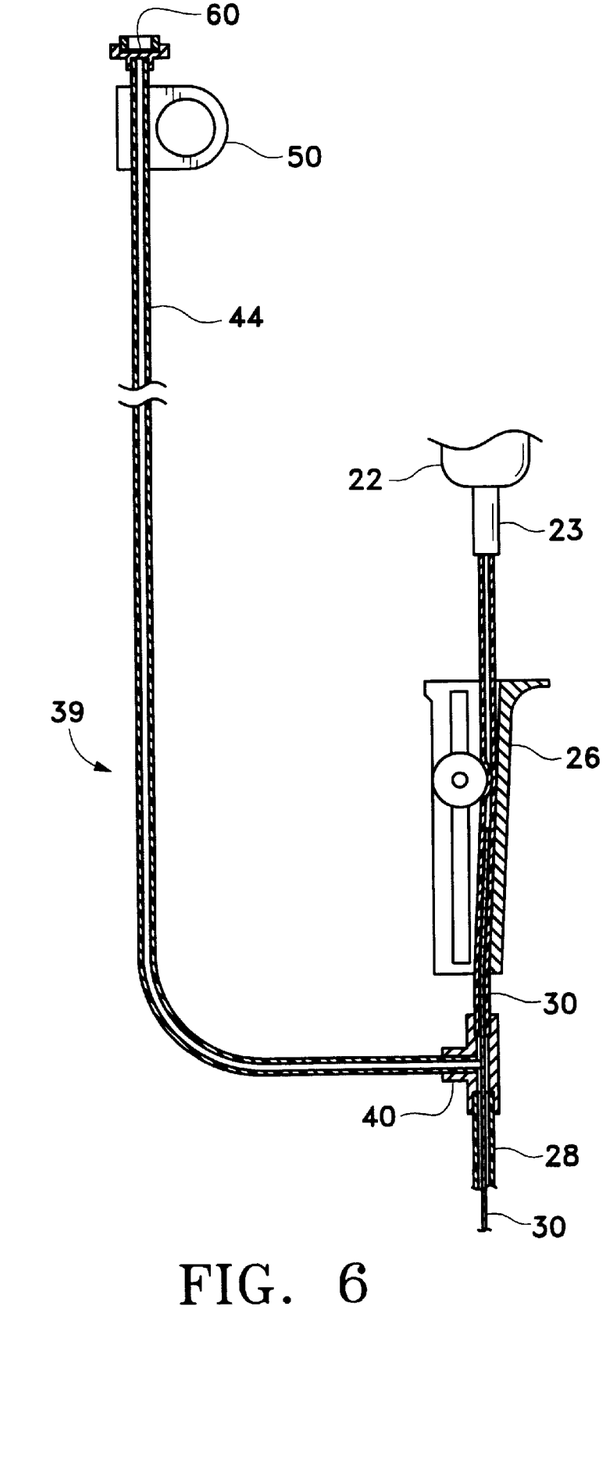
FIG. 6 is a cross sectional side elevation of a venting system of FIG. 1.
Figure 7:
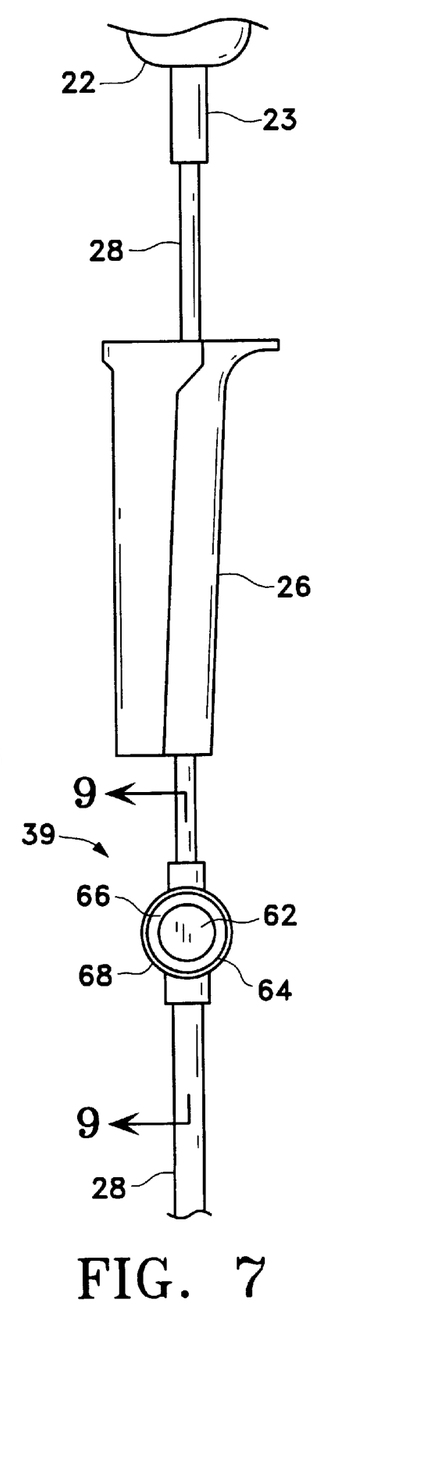
FIG. 7 is a front elevation of an alternative venting system for use with the present invention of FIG. 1.
Figure 8:
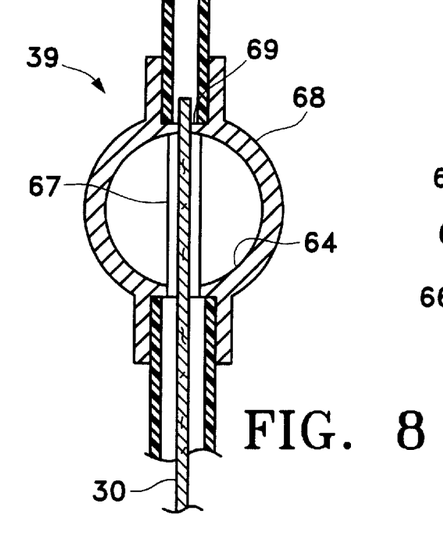
FIG. 8 is a cross sectional front elevation of the venting system of FIG. 7 taken along lines 8—8 of FIG. 7.
Figure 9:
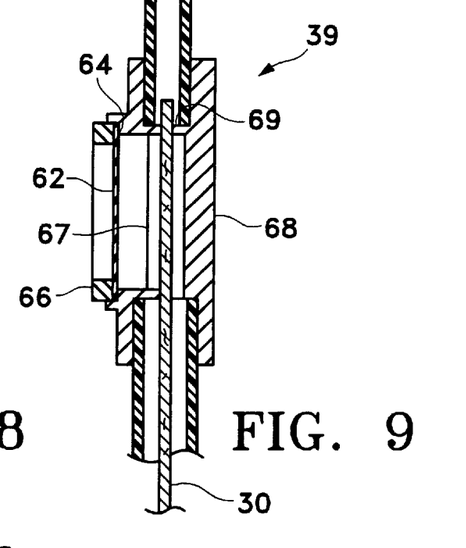
FIG. 9 is a cross sectional side elevation of the venting system of FIG. 7.

Now referring to FIG. 1 and to FIG. 6, the vent 39 includes a bacteria filtering air filter 60 at its distal end. If a condition develops that stops or nearly stops the flow of liquid out of the regulating tube 28, such as a pinched transport tube, the standing column height of liquid in the regulating tube will rise until the vent tube tee 42 fills with liquid. Then isolation of the pressure drop across the tube clamp 26 is lost and liquid will flow upward into the vent tube 44 forming a standing column of liquid in the vent tube 44. This standing column will tend to rise until its height is the same as the height of the liquid level in the I.V. bag 22, or runs out of the end of the vent tube 44. To prevent the latter result, in the embodiment illustrated in FIGS. 1, 6, the vent tube 44 is long enough so that its distal end 48 can be and is placed higher than the top of the I.V. bag 22. Alternatively a gas permeable hydrophobic membrane 62 is secured across a vent port 64, by a retaining ring 66 which is fastened to the vent housing 68 by sonic welding, gluing, or the like, eliminating the vent tube 44 to seal the gas permeable hydrophobic membrane 62 over the vent port 64 of the vent housing 68. The gas permeable hydrophobic membrane 62 allows air to flow freely in and out of the regulating tube 28, but prevents any liquid from leaking out of the vent tee 40. The wick 30 passes through a channel 67 within the vent 39 of FIGS. 7–9 that helps collect and flow any liquid protruding from the wick into the lower tube without having the liquid contact the membrane 62, which helps prevent the internal liquid from interfering with the air flow into and out of the bottom tube. Unrestricted air transfer from the bottom tube to the vent 39 is required for best performance. The portion of the regulating tube 28 exiting from the bottom of the vent 39 is slightly larger than the width and depth of the channel 67. In this embodiment, the wick 30 does not run up past the roller of the tube clamp 26. Rather the top portion of the wick 30 is secured in an orifice 69 in the upper portion of the vent housing 68. The orifice 69 is sized to limit the maximum liquid flow through the vent 39 to maintain the liquid flow within the design limits. In either case, once normal flow conditions are restored, the height of the standing column of liquid in the regulating tube 28 falls to the height required for the flow conditions and steady state liquid control resumes.

The pressure drop across the tube clamp 26 is isolated from downstream pressure conditions by the vent 39. The vent 39 allows the liquid flow through the tube clamp 26 to flow at atmospheric pressure. A stream of liquid 43 (FIG. 2) runs down the interior side wall 52 of the transport tube 28 until it reaches the standing column of liquid 54 in the regulating tube 28. The height of the standing column of liquid 54 automatically fluctuates up and down until the pressure head generated by the standing column of liquid 54 insures that the rate of exiting liquid flow from the regulating tube 28 is equal to the incoming liquid flow. It is advantageous to make the internal volume of the regulating tube 28 as small as possible so that the accumulation effect of the regulating tube 28 is reduced. When a change in downstream flow condition occurs, for example, when the patient 41 sits up, the height of the standing column of liquid 54 in the regulating tube 28 must change to a different level to insure a steady state liquid flow rate through the intravenous liquid flow regulator 10 into the patient 41. The rate of change of the height of the standing column of liquid 54 is directly proportional to the rate of liquid flow in, minus liquid flow out, divided by the cross sectional area of the regulation tube's internal diameter. The smaller the cross sectional area of the regulating tube, the faster the standing column height will change, and the quicker the intravenous liquid flow regulator 10 will come into steady state condition. The pressure head resident in the standing column of liquid 54 provides the regulating force to deliver a constant flow rate through the intravenous liquid flow regulator 10 and hence into the patient 41.

Reducing the internal diameter of the regulating tube 28, however, disrupts the flow of liquid down the internal side wall 52 and leads to drops of liquid forming on the internal side wall 52. Once the drops become large enough to bridge the internal diameter of the regulating tube 28, they do so, trapping air below the drops. If this occurs unchecked, a mixture of liquid and air slowly accumulates in the regulating tube 28, interfering with the correct liquid flow control.

Figure 3:
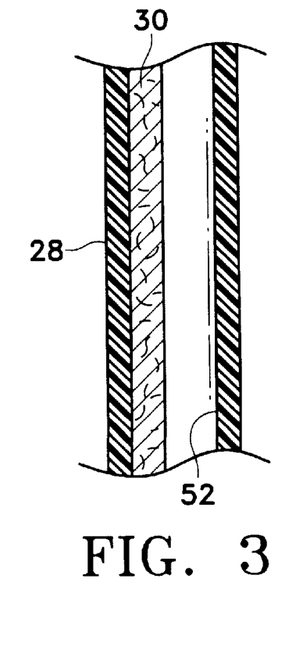
FIG. 3 is a cross sectional side elevation of the regulating tube of FIG. 1 showing use of a wick to prevent bubble formation.
Figure 4:
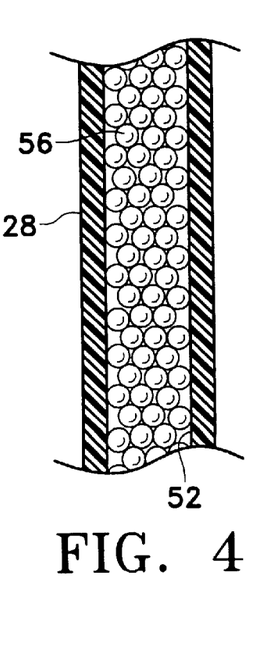
FIG. 4 is a cross sectional side elevation of an alternative embodiment of the regulating tube of FIG. 1.
Figure 5:
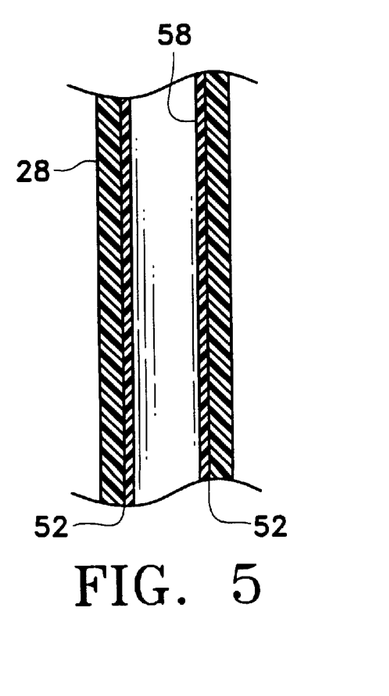
FIG. 5 is a cross sectional side elevation of an another alternative embodiment of the regulating tube of FIG. 1.

To prevent drops of liquid from forming on the interior side wall 52 of the transport tube 28, an internal wick 30 is added to the inside of the regulating tube 28, as shown in FIG. 3. The wick 30 occupies a fraction of the internal cross sectional area of the regulating tube 28 lying in a range of one-quarter to three-quarters of the cross sectional area., with one-third being the preferred ratio. The wick 30 breaks the surface tension of the liquid as it flows down the internal side wall 52 of the regulating tube 28, thereby preventing large drops of liquid from occurring within the regulating tube 28. The wick 30 may be made of any of a number of suitable materials that absorb and transport liquid, that is, that allow liquid to flow through it. A preferred material for the wick 30 is medical grade cotton. Alternatively, as shown in FIG. 4, the internal volume of the regulating tube 28 may be more or less filled with small beads 56 made of glass or plastic and in any desired colors. The beads 56 also break the surface tension of the liquid flowing through the regulating tube 28, thereby reducing the likelihood that bubbles will form in the liquid flowing through the regulating tube 28. Referring to FIG. 5, another alternative bubble reduction system includes making the interior surface of the regulating tube 28 slippery, such as by coating the interior surface with a slick material on the internal side wall 52 of the regulating tube 28, which in FIG. 5 is a coating of polytetrafluoroethene 58.

Figure 10:
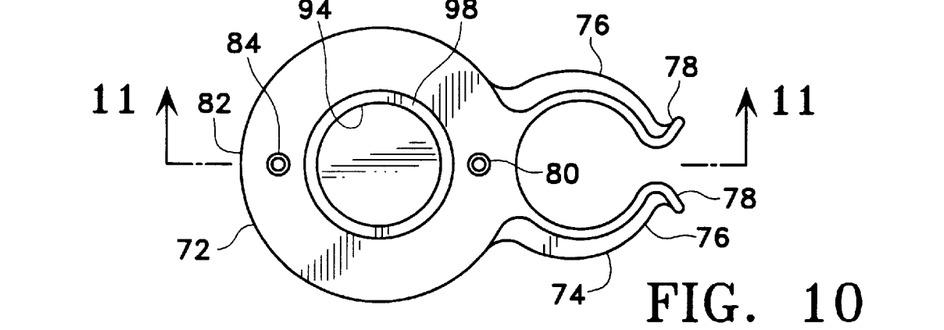
FIG. 10 is a top plan view of one embodiment of a bubble separator component of the intravenous liquid flow regulator according to the present invention.
Figure 11:
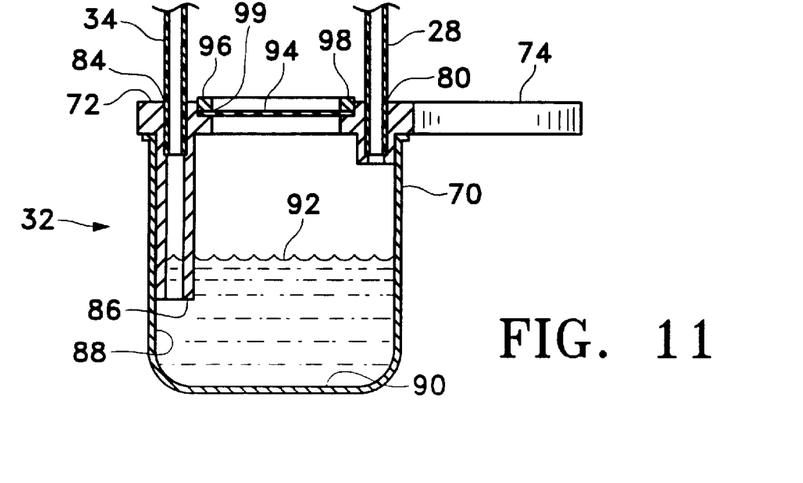
FIG. 11 is a sectional side elevation of the bubble separator of FIG. 10 taken along lines 11—11 of FIG. 10.

Referring now to FIGS. 10, 11, a preferred embodiment of the bubble separator 32 includes a housing or container 70 consisting of a container, having a cover 72 that includes a clamp bracket 74 connected or formed therein, which is snapped onto the I.V. stand 12 near the floor 16 (FIG. 1), to insure that the bubble separator 32 is retained in an upright position, that is the position shown in FIGS. 1 and 11, which is necessary to its proper operation. The clamp bracket 74 includes a pair of opposed symmetrical curved semi-circular arms 76, each having a distal outwardly turned end portion 78. The clamp bracket comprises a pair of opposed inwardly curved arcuate arms adapted for clamping about a cylindrical form. When they are pushed against the I.V. stand 12, the outwardly turned end portions 78 are wedged outwardly, expanding the distance between the curved semi-circular arms 76 and allowing the I.V. stand 12 fit between them. Then the elastic nature of the curved semi-circular arms 76 snaps them closer together into a firm frictional engagement with the I.V. stand 12, retaining the bubble separator 32 in the desired position on the I.V. stand 12 adjacent to the floor 16.

Still referring to FIGS. 10, 11, the regulating tube 28 is inserted into an entrance tube receiving port 80 adjacent to one edge of the cover 72. Across a diameter of the cover 72, adjacent to the edge 84 of the cover 72, the transport tube 34 leading to the patient 41 is inserted into a transport tube receiving port 84, which is sealed to and connected to an extension tube 86 fixed to the adjacent interior side wall 88. The extension tube 86 extends downwardly to a level adjacent to but somewhat above the bottom wall 90 to insure that the transport tube 34 draws fluid only from below the level of the liquid 92 in the bubble separator 32 at all times.

Still referring to FIGS. 10, 11, a gas permeable hydrophobic membrane is seated in a seat 96 in the cover 72 about an opening 99 in the cover and is held in place by a ring membrane retainer 98. The bubble separator 32 is preferably made from plastic and the different pieces, including the ring membrane retainer 98 are held in place by chemical or sonic welding.

Any bubbles that may have become entrained in the liquid flowing through the regulating tube 28 are removed in the bubble separator 32. No liquid can be transported to the transport tube 34 until enough accumulates in the container 70 to cover the lower end of the extension tube 86. Any bubbles entrained in the liquid flowing through the regulating tube 28 naturally float to the upper surface of the liquid in the container 70. The pressure head from the standing column of liquid 54 is sufficient both to force the air through the gas permeable hydrophobic membrane 94 and to force liquid through the transport tube 34 and into the patient 41. During normal use, the container 70 fills but the liquid cannot escape from the bubble separator 32, because it will not penetrate the membrane 94.

Figure 12:
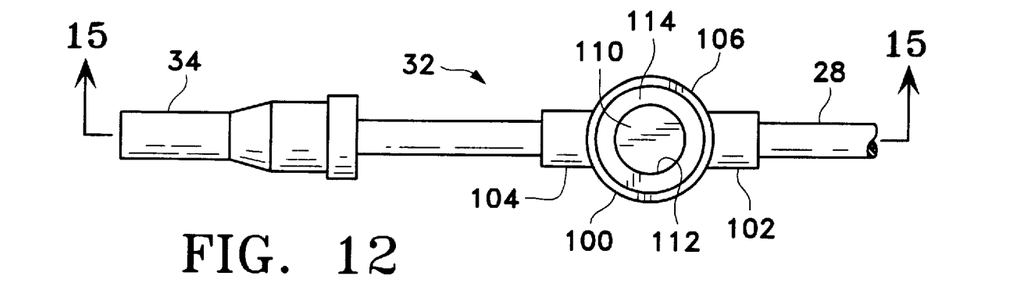
FIG. 12 is a top plan view of an alternative embodiment of a bubble separator.
Figure 13:
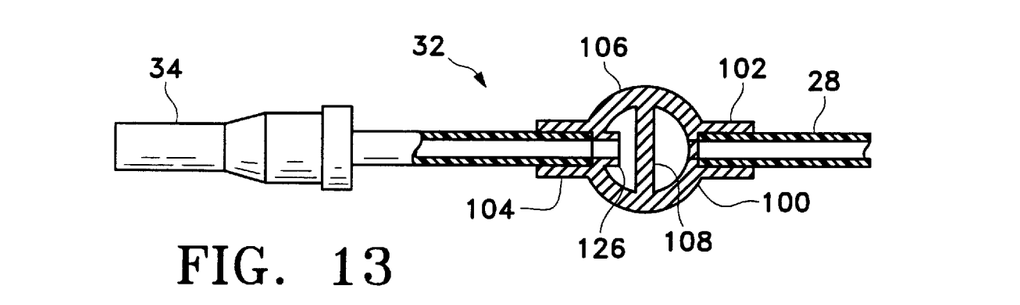
FIG. 13 is a cross sectional view of the bubble separator of FIG. 12 taken along lines 13—13 of FIG. 12.
Figure 14:
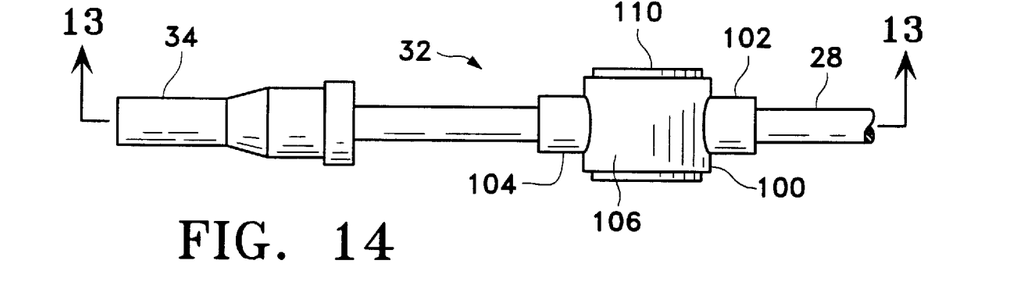
FIG. 14 is a side elevation of the bubble separator of FIG. 12.
Figure 15:
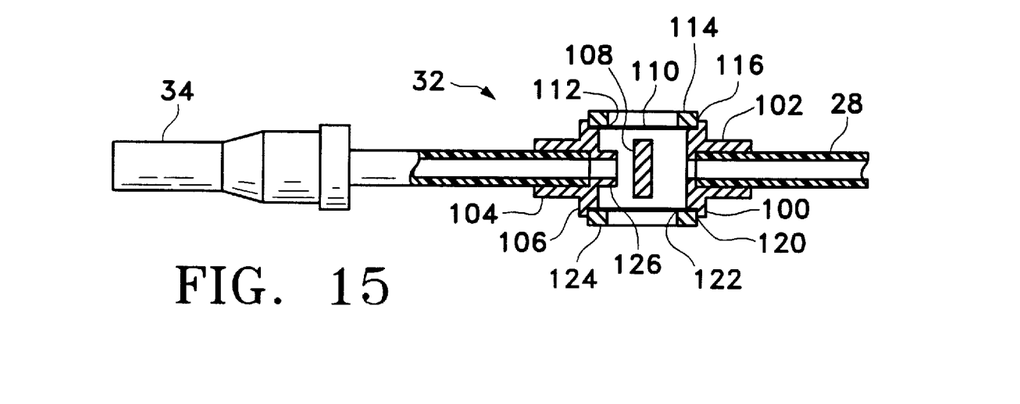
FIG. 15 is a cross section of FIG. 14 taken along lines 15—15 of FIG. 14.

The embodiment of the bubble separator 32 discussed above in conjunction with FIGS. 10, 11 must be positioned in an upright position, that is, with the gas permeable hydrophobic membrane 94 at the highest point of the bubble separator 32 to insure that entrained gas will be forced out of the liquid before being transported to the patient 41. The embodiment of the bubble separator 32 illustrated in FIGS. 12–15 overcomes this disadvantage by providing a bubble separator 32 that will operate to remove entrained bubbles from a flow of liquid regardless of the orientation in space of the bubble separator 32. In this embodiment, the bubble separator 32 is smaller than the embodiment of FIGS. 11 and 12 and may placed in the transport tube 34 nearer to the patient 41, but upstream of the check valve 36, without regard to orientation up or down.

Referring to FIGS. 12–15 a housing 100 includes a regulating tube receiving orifice or port 102 at a right-hand end and a transport tube receiving orifice or port 104 at the left-hand end for sealing frictional engagement of the respective tubes 28, 34. A substantially cylindrical central chamber 106 having a flow deflector or baffle 108 across a diameter of the central chamber 106 perpendicular to the direction of flow through the bubble separator 32. The flow deflector 108 lies along a central span from top to bottom of the chamber 106, with the top of the chamber 106 as defined herein being the upper part of FIGS. 14 and 15. The flow deflector 108 insures that no bubbles can pass directly from the entrance port 102 to the exit port 104 by blocking the direct path between them. An upper gas permeable hydrophobic membrane 110 is sealed into an upper membrane aperture 112 by a ring membrane retainer 114. The membrane 110 is seated about a circumferential seat 116 formed into the top of the housing 100 and ring membrane retainer 114 is seated and sealed on the membrane 110. A lower gas permeable hydrophobic membrane 118 is seated into a lower membrane circumferential seat 120 and covers the lower membrane aperture 122. The lower membrane 118 is sealed into position by the lower ring membrane retainer 124. The transport tube receiving orifice or port 102 extends into the central chamber 106 by an amount in the range of one-fourth to one-third of the diameter of the central chamber 106, and forms an exit tube extension 126, which helps prevent any air that may have been collected on the top membrane (whichever one that may be with the bubble separator 32 in a particular orientation) from entering the exit port 104 when the orientation of the bubble separator 32 shifts suddenly. Any air in the bubble separator 32 will follow the walls of the bubble separator 32 when it is shifted to a different orientation.

Air bubbles do not normally form in the regulating tube 28, as explained above. If, however, the regulating tube 28 is pinched or clamped at a point above the standing column of liquid 54, bubbles may develop, even though the wick 30 eliminates most of these problems. It remains, however, possible, that an air bubble may become entrained in the liquid flow and flow out of the regulating tube 28, from where it could possibly enter the patient 41. The bubble separator discussed above is designed to remove any such bubbles and insure that no bubbles reach the patient 41. Fluid velocity inside the bubble separator 32 is low or stagnate, allowing the air to float to the top of the container. In the embodiment of FIGS. 11–15, separate gas permeable hydrophobic membranes are located in at least two places on the bubble separator 32, so that no matter what the orientation in space of the bubble separator 32, one or more membranes will be near enough to the highest point on the bubble separator 32 to permit any entrained air to escape to the atmosphere.

The gas permeable hydrophobic membranes used herein must be large enough that the largest expected volume of entrained air entering the bubble separator 32 can be vented at the expected head pressure of the intravenous liquid flow regulator 10. The shape and size of the container portion of the bubble separator must be large enough to insure that the fluid velocity inside the container is low or stagnate so that entrained air bubbles have time to be displaced to the top of the container for venting to the atmosphere. Similarly, the liquid path through the container must insure that the passing liquid is retained inside the container long enough for the air to be displaced out of the liquid stream exiting the container. The end of the exit tube inside the container must always be covered with liquid during use.

The intravenous liquid flow regulator is made from surgical grade plastic, silicon, injected molded plastic, extruded plastic, and the like. The components are attached to one another by gluing, sonic welding, and the like, except the tubing, which is typically friction fitted over coupling members. The intravenous liquid flow regulator may be provided as a disposable unit similar to currently used I.V. administration sets, or may be made for sterilization and reuse.

Different models of the intravenous liquid flow regulator provide different optimal flow ranges for use when different transient response requirements. Convenient flow rate ranges are 0–10 ml/hr; 0–100 ml/hr; and 0–1,000 ml/hr.

While the present invention has been described in accordance with the preferred embodiments thereof, the description is for illustration only and should not be construed as limiting the scope of the invention. Various changes and modifications may be made by those skilled in the art without departing from the spirit and scope of the invention as defined by the following claims.

I claim:

1. An apparatus for regulating flow through an I.V. set comprising:
   a. a depending regulating tube connected to an I.V. container, said regulating tube having an upper end and a lower end;
   b. means for venting said regulating tube located proximate to said upper end of said regulating tube and at the top of said I.V. container; and
   c. means for preventing the formation of drops of liquid in said regulating tube.

2. An apparatus for regulating flow through an I.V. set according to claim 1 wherein said drop prevention means further comprises means for making an interior surface of said regulating tube slippery.

3. An apparatus for regulating flow through an I.V. set according to claim 2 wherein said means for making said interior surface of said regulating tube slippery further comprises coating said interior surface with polytetrafluoroethene.

4. An apparatus for regulating flow through an I.V. set according to claim 1 wherein said drip prevention means further comprises filling said interior of said regulating tube with a plurality of spherical beads.

5. An apparatus for regulating flow through an I.V. set according to claim 1 wherein said means for preventing the formation of drops of liquid in said regulating tube further comprises a wick inside said regulating tube.

6. An apparatus for regulating flow through an I.V. set according to claim 5 wherein said wick further comprises a cotton wick.

7. An apparatus for regulating flow through an I.V. set according to claim 1 wherein said means for venting said regulating tube further comprises a vent tube having a proximal end inserted into said regulating tube proximate to said upper end of said regulating tube and a vent filter at a distal end of said vent tube, with said vent filter being disposed at a point not lower than the top of said I.V. container.

8. An apparatus for regulating flow through an I.V. set according to claim 1 wherein said means for venting further comprises a housing having a vent port and a gas permeable hydrophobic membrane sealed over said vent port with said housing being disposed at a point not lower than the top of said I.V. container.

9. An apparatus for regulating flow through an I.V. set comprising:
   a. a depending regulating tube connected to an I.V. container said regulating tube having an upper end and a lower end;
   b. means for venting said regulating tube proximate to said upper end; and
   c. means for preventing the formation of drops of liquid in said regulating tube; and means for separating entrained bubbles from the liquid flowing through said regulating tube, wherein said means for separating entrained bubbles further comprises a housing having an inlet tube and an outlet tube and at least one sealed gas permeable hydrophobic membrane covering at least one vent port.

10. An apparatus for regulating flow through an I.V. set in accordance with claim 9 wherein said inlet tube is connected to an extension tube and said extension tube projects into said housing.

11. An apparatus for regulating flow through an I.V. set comprising:
   a. a depending tube connected to an I.V. container, said tube having an upper end and a lower end; and
   b. means for separating entrained bubbles from the liquid flowing through said tube connected to said tube at a location proximate to said lower end said means for separating entrained bubbles further comprising a housing having an inlet tube and an outlet tube and at least one sealed gas permeable hydrophobic membrane covering at least one vent port.

12. An apparatus for removing bubbles in a flow through an I.V. set according to claim 11 wherein said means for separating entrained bubbles further comprises a housing having a bottom wall connected to upstanding side walls and a cover having an opening therein covered by a gas permeable hydrophobic membrane and means for transporting liquid through said housing.

13. An apparatus for removing bubbles in a flow through an I.V. set according to claim 12 wherein said liquid transporting means further comprises a regulating tube receiving port in said cover and a transport tube receiving port in said cover and an extension tube connected to said transport tube receiving port and projecting into said housing to a point adjacent to said bottom wall of said housing.

14. An apparatus for removing bubbles in a flow through an I.V. set according to claim 12 wherein said cover further comprises a clamp bracket comprising a pair of opposed inwardly curved arcuate arms adapted for clamping about a cylindrical form.

15. An apparatus for removing bubbles in a flow through an I.V. set according to claim 11 wherein said means for separating bubbles further comprises a regulating tube orifice connected to a central chamber, a transport tube receiving orifice connected to said central chamber, at least two membrane apertures, each covered by a separate gas permeable hydrophobic membrane and a flow deflector inside said central chamber.

16. An apparatus for removing bubbles in a flow through an I.V. set according to claim 15 wherein said means for separating bubbles further comprises axial alignment of said regulating tube orifice and said transport tube receiving orifice.

17. An apparatus for removing bubbles in a flow through an I.V. set according to claim 15 further comprising a circumferential seat about each membrane apertures and a ring membrane retainer sealing each said gas permeable hydrophobic membrane in each said seat and over each said membrane aperture.

18. An apparatus for removing bubbles in a flow through an I.V. set according to claim 15 wherein said flow deflector further comprises a baffle across said central chamber between said transport tube receiving orifice and said transport tube receiving orifice, said baffle having a width larger than the diameters of said transport tube receiving orifice and of said transport tube receiving orifice.

\* \* \* \* \*